United States Patent [19]

Bhatt et al.

[11] Patent Number: 4,581,339

[45] Date of Patent: Apr. 8, 1986

[54] CATALYTIC DEHYDROGENATION REACTOR CYCLE

[75] Inventors: Bharat L. Bhatt, Fogelsville; John F. Kirner; Pradip Rao, both of Allentown; William A. Schwartz, Fogelsville, all of Pa.

[73] Assignee: Air Products and Chemicals, Inc., Allentown, Pa.

[21] Appl. No.: 712,831

[22] Filed: Mar. 18, 1985

[51] Int. Cl.$^4$ .................... B01J 38/12; C07C 5/327
[52] U.S. Cl. ............................ 502/38; 502/41; 502/47; 502/50; 502/51; 502/52; 585/654; 585/658; 585/662; 585/663
[58] Field of Search ............... 502/38, 41, 46, 47, 502/50, 51, 52; 585/658, 662, 663, 654, 657

[56] References Cited

U.S. PATENT DOCUMENTS 3,647,909 3/1972 Michaels et al. .................. 502/38

FOREIGN PATENT DOCUMENTS 1398086 6/1975 United Kingdom .................. 502/50

OTHER PUBLICATIONS

The Catadiene Process, R. G. Craig, et al., Chemical Engineering Progress, Feb. 1979, pp. 62–65.
Dehydrogenation Links LPG to Mere Octanes, S. Gussow, et al., Oil & Gas Journal, Dec. 8, 1980, pp. 96–101.

Primary Examiner—John Doll
Assistant Examiner—A. Pal
Attorney, Agent, or Firm—Mark L. Rodgers; E. Eugene Innis; James C. Simmons

[57] ABSTRACT

A method for reheating of a catalytic reactor by successive oxidations and reductions of a multiple oxidation state catalyst.

Heat is added to the catalyst bed by a series of successive oxidation and reduction reactions occurring on the catalyst. Both catalyst oxidation and catalyst reduction are exothermic reactions, and both reactions generate heat to increase the temperature of the catalyst bed.

15 Claims, 6 Drawing Figures

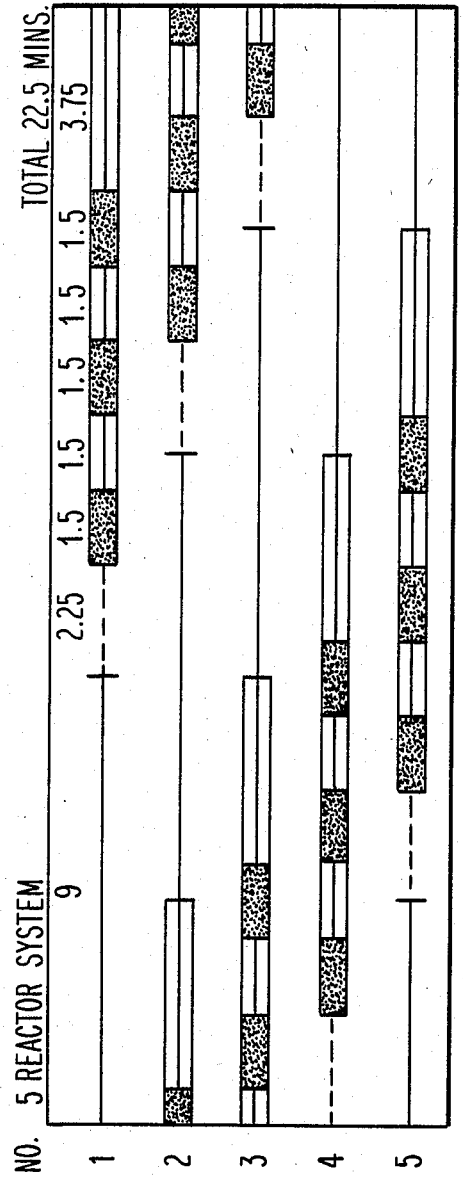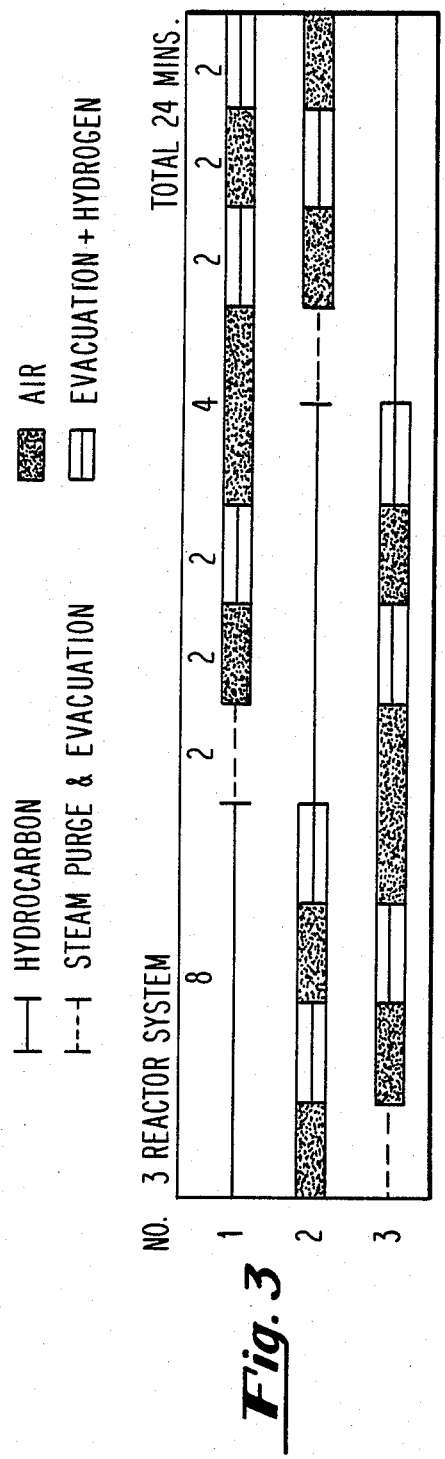

CATALYTIC DEHYDROGENATION REACTOR CYCLE

FIELD OF THE INVENTION

The present invention is directed to a method of operation of a catalytic dehydrogenation reactor system for the production of light olefins from parafins.

BACKGROUND OF THE INVENTION

The production of $C_2$–$C_5$ olefins from liquified petroleum gas (LPG) by catalytic dehydrogenation involves the use of cycled catalytic reactors. Reactors containing a catalytic bed in the form of cylindrical pellets of chromic oxide on active alumina support are typically used to dehydrogenate LPG feed materials which are then compressed and separated to yield desired products including propylene, isobutylene, other butenes and pentenes, light hydrocarbon gases, and hydrogen gas. Typical of such a reaction system is the Catofin TM-/Catadiene TM system. The general reaction catalyzed within the system is the dehydrogenation of alkane hydrocarbons to alkenes.

$$C_nH_{(2n+2)} \rightarrow C_nH_{2n} + H_2 \tag{I}$$

This dehydrogenation of LPG to produce olefins is a highly endothermic reaction. For example, approximately 1,000 BTUs must be supplied per pound of product double bond produced for $C_4$ compounds and about 1,300 BTUs must be supplied per pound of product double bond for the propane-to-propylene reaction. The needed reaction heat is primarily supplied by heat stored in the catalyst bed which is heated in an off-stream part of the cycle.

The Catofin TM and Catadiene TM processes are described in numerous publications including Craig, R. G. et al, *Chemical Engineering Progress*, February, 1979 pp. 62–65 and Gussow, S. et al, *Oil & Gas Journal*, Dec. 8, 1980 pp. 96–101.

The prior art methods of reactor reheating include the combustion of coke deposited on the catalyst during the dehydrogenation reaction. This deposited coke was burned with preheated air to heat the catalyst bed to the desired temperature. Additionally, fuel gas may be burned in the reactor to provide additional energy. Another source of the heat required by the dehydrogenation reaction is the sensible heat of air which is pumped through the reactor.

Once reheated to the desired temperature, a reactor was cycled for a short time with hydrogen to reduce the catalyst and placed on-stream where the endothermic dehydrogenation reaction absorbed the energy, decreasing reactor temperature during the on-stream period.

This reactor cycle included a steam purge of the reactor to remove hydrocarbon materials, evacuation of the reactor, reheating with air or air and fuel gas mixture concurrently with coke combustion to heat the reactor to the desired temperature, post-reheat evacuation, exposure to a reducing gas, and resumption of dehydrogenation processing. In order to provide continuous major process stream flows, at least two reactors are needed. Commercially, systems of three to eight reactors are commonly employed. A central timing device programs the cycle sequence for reactor reheat, purge, and operation phases.

Prior art methods for reheating the catalytic reactor have several demonstrated shortcomings. When operated with higher fractions of non-diolefin-forming hydrocarbons, the amount of coke deposited on the catalyst bed during the on-stream period is generally insufficient to provide needed energy during the reheat cycle.

Furthermore, newer, more efficient dehydrogenation catalysts yield less coke than older catalyst types for equal amounts of product olefin produced. Thus, systems using these new catalysts require alternative sources of energy during the reheat cycle. This additional energy must be supplied by heating air to very high temperatures or by burning light hydrocarbon fuel gases in the reactor. Both alternatives are undesirable.

Whether additional heating of the recycle air stream or fuel gas combustion in the reactor is employed, excessive temperatures may be encountered at the top of the bed, leading to catalyst deactivation. In addition, uneven catalyst heating leads to cooler spots as well as areas of deactivated catalyst, both of which degrade process performance.

Reheating of the catalyst bed by heated air, burning of coke, or burning of fuel gas also carries with it the added disadvantage of introducing a thermal gradient to the bed. During reheat, the top of the bed will heat first and most rapidly, while the lower regions will heat slowly. Because catalyst deactivation is a primary limit on the reheating cycle, the reheat must be stopped when the top of the bed reaches maximum allowable temperatures. At these conditions, the bottom of the catalyst bed is generally far below its optimum temperature.

When placed back on-stream, this thermal gradient causes enhanced activity at the top of the bed and reduced efficiency toward the bottom. As a result, greater amounts of coke are deposited at the top, which in turn leads to a perpetuation of the undesirable thermal gradient during subsequent reheating cycles.

BRIEF DESCRIPTION OF THE FIGURES

FIG. 3 is a timeline diagram of the operational cycle of a three-reactor system according to the present invention.

FIG. 4 is a timeline diagram of the operational cycle of a five-reactor system according to the present invention.

BRIEF DESCRIPTION OF THE INVENTION

According to the present invention, a fixed bed, adiabatic catalytic dehydrogenation reactor such as that employed in the Catofin TM and Catadiene TM processes for the production of $C_2$–$C_5$ olefins is regenerated after an on-stream period by introducing (a) an oxidizing gas (typically air, optionally with an added fuel gas to burn for in-situ heat generation) heated to 1000°–1300° F. for a first predetermined period of time sufficient to burn substantially all coke within the reactor and (b) for a second predetermined period of time to effect some oxidation of the catalyst itself; and then (c)

a reducing gas (typically hydrogen, optionally containing 10-25 mol% light hydrocarbons) also heated to 1000°-1300° F., for a third predetermined period of time to return the catalyst to a lower oxidation state. Regeneration then continues by one or more cycles including introducing (d) oxidizing gas again at 1000°-1300° F. for a fourth predetermined period of time sufficient to re-oxidize the catalyst; and (e) reducing gas at 1000°-1300° F. for the predetermined period of time necessary to again reduce the catalyst to a lower oxidation state. This cyclic process is repeated until the catalyst bed temperature reaches or approaches the desired reactor operating temperatures, generally on the order of 1000°-1150° F.

The catalyst bed temperature increases due to the exothermic oxidation and reduction reactions taking place on the catalyst. Both catalyst oxidation and catalyst reduction are exothermic reactions, and therefore, heat is provided to the catalyst bed by each oxidation step and by each reduction step.

DETAILED DESCRIPTION OF THE INVENTION

Figure 1:
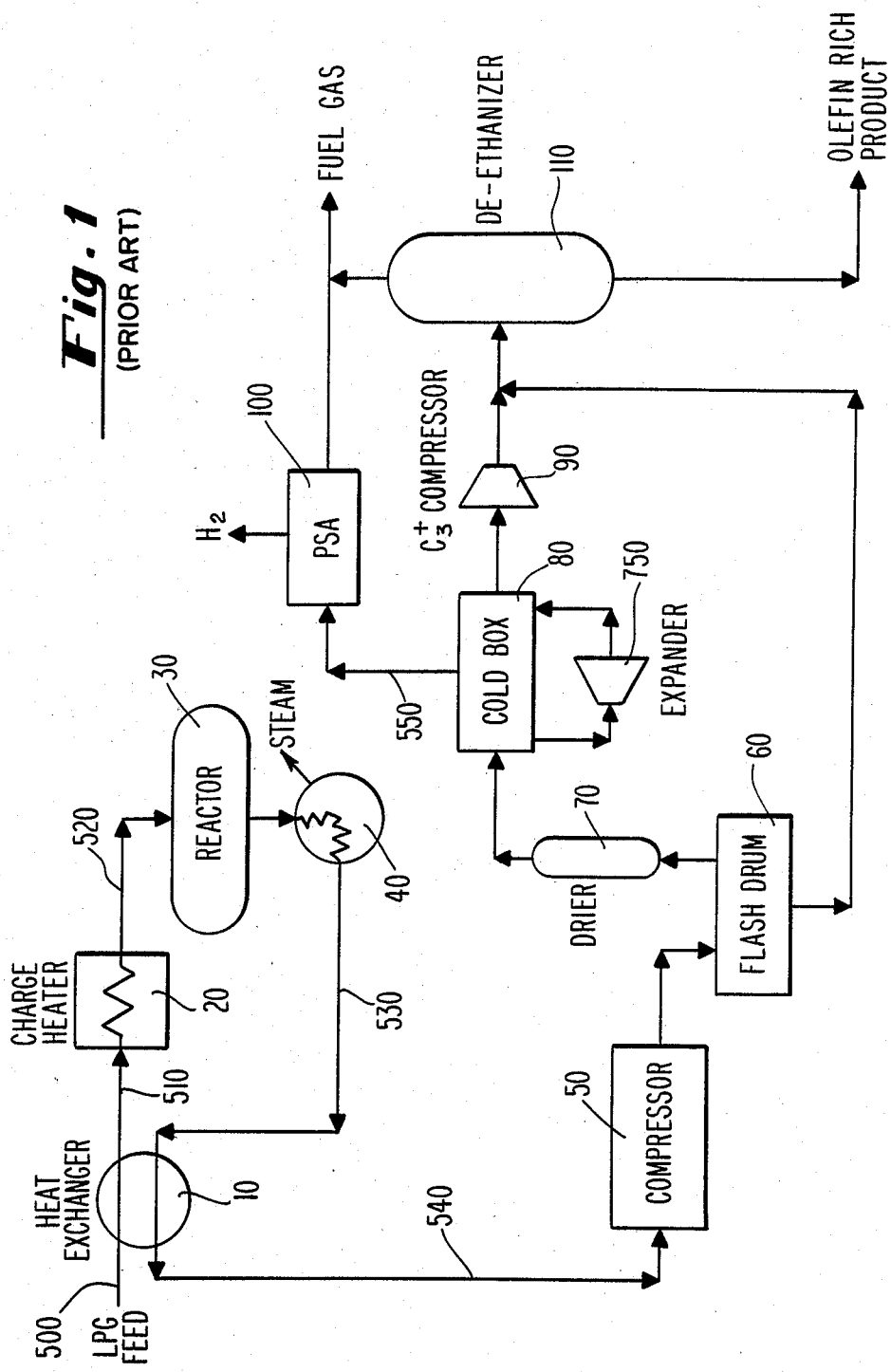
FIG. 1 is a flow diagram of the prior art catalytic dehydrogenation process including the product recovery section.

Referring now to FIG. 1, which depicts the material flows within the Catofin TM process system, liquified petroleum gas feed stocks enter the process via line 500 and are preheated by thermal contact with a reactor effluent stream within heat exchanger 10. After preheating, the feed stocks are transferred via line 510 to charge heater 20 where they are heated to a higher temperature, on the order of 1200° F., by additional energy input such as fuel gas combustion. Heated feed stocks are transferred via line 520 to catalytic reactor 30 for dehydrogenation.

Catalytic reactor 30 contains a bed of active dehydrogenation catalyst having multiple oxidation states. For example, catalysts comprising cylindrical pellets of active alumina impregnated with 18-20% chromic oxide, and optionally mixed with a proportion of tabular alumina are typically employed.

After dehydrogenation to form olefin products, reactor effluent stream 530 is cooled by steam generation within steam generator 40 and further cooled by contact with LPG feed stock materials in heat exchanger 10. Reactor effluent is then transferred via line 540 to compression train 50. Compressed reactor effluent is then flashed in flash drum 60 to separate light ends from heavier $C_4$ and $C_5$ olefins. These light ends are dried within dryer 70 and subsequently separated within cold box 80 into a stream comprising primarily $C_3$ olefins and a stream comprising hydrogen and light gases. $C_3$ olefins are compressed within compressor 90 and fed together with flash bottoms from flash drum 60 to deethanizer 110. Light gases may optionally be transferred from cold box 80 to pressure swing adsorbtion unit 100 via line 550. Pressure swing adsorbtion unit 100 separates hydrogen gas from light hydrocarbons. Deethanizer 110 similarly separates light hydrocarbons from $C_3$-$C_5$ olefins which are recovered as product.

Figure 2:
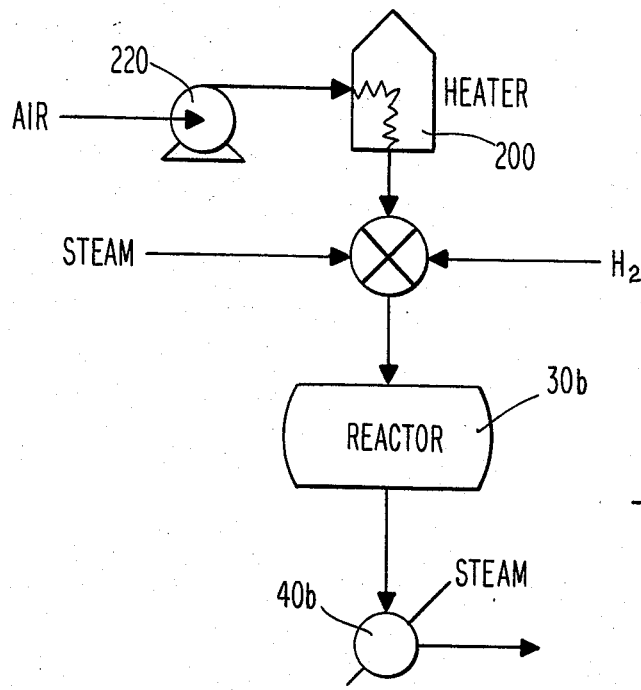
FIG. 2 is a schematic diagram of the catalytic reactor reheat process of the present invention.

Referring now to FIG. 2, there is shown a regeneration system flow diagram. Catalytic reactors employed in the Catofin TM and Catadiene TM processes are regenerated off-stream. According to the prior art, after the on-stream period, these reactors are first steam purged and evacuated to remove residual hydrocarbons. Air compressed within compressor 220 and heated to a temperature of from 1000° F. to 1300° F. within heater 200 is then introduced into the reactor.

Coke deposited within the reactor during the production cycle is allowed to burn, raising the temperature of the catalyst bed. In addition, fuel gas (typically 75-90 mol% $H_2$ mixed with light hydrocarbons) may be introduced to the reactor and allowed to combust, thereby providing greater energy input. At the same time, the catalyst is converted to a higher oxidation state.

Subsequently, small amounts of reducing gas (fuel gas) are fed into the reactor prior to placing the regenerated reactor back on-stream at a bed temperature of 1000°-1150° F.

According to the preferred form of the present invention, the reactor regeneration procedure is expanded to include several alternating cycles of preheated oxidizing and reducing gas, as well as purging and evacuation of the reactor 30b. In these cycles, after the first, the time of the oxidizing phase of the cycle will be somewhat less than in the first such oxidization step when the time must be sufficient to burn coke from the catalyst as well as to oxidize the catalyst. The duration and number of such cycles may be adjusted to optimize the temperature and temperature profile of a given reactor within a system and to provide continuous major stream flows within a complete system.

The reducing gas can either have a downflow or have an upflow. The upflow can be achieved by placing the reactor evacuation outlet line above the catalyst bed and by adding the reducing gas below the bed. An upflow of reducing gas may beneficially reduce the temperature gradient which commonly occurs in the catalyst bed.

In a system having three reactors, the process cycle may appear as represented in FIG. 3. FIG. 3 comprises a staggered cycle of eight minutes' on-stream operation followed by two minutes of reactor steam purge and evacuation, two minutes of air flow through the reactor, evacuation followed by two minutes of reducing gas flow, four minutes of air flow, another two minutes of evacuation and reducing gas flow, a further two-minute air flow, and a final evacuation and reducing gas flow to set the oxidation state of the catalyst. One complete cycle requires 24 minutes and one reactor will be on-stream at any given time.

In a five-reactor system, the scheme depicted in FIG. 4 may be employed. This 22.5-minute cycle permits two reactors to remain in production at all times, while the remaining three are in various stages of the regeneration cycle.

Although air and reducing gas cycling of the reactor were known in the prior art, this cycling was used primarily to raise reactor temperatures by burning coke and by transferring the sensible heat of the air to the catalyst. Of course, some catalyst oxidation by the air occurred, but such oxidation was a minimal contributor to the overall heating of the reactor. In addition, hydrogen flows were used merely to reduce the catalyst to minimize the waste of hydrocarbon feedstocks, and not for significant contribution to reactor heating. In systems which produced relatively little coking of the catalyst bed, these techniques (specifically, the burning of coke) were ineffective to reheat the off-stream reactor, and were supplemented with additional heating by air and/or burning of fuel gas in the reactor.

In accordance with the present invention, the catalyst bed temperature is increased by successive oxidation and reduction reactions taking place on the catalyst. Both catalyst oxidation and catalyst reduction are exothermic reactions and, therefore, heat is provided to the catalyst bed by each oxidation step and by each reduction step.

During the oxidation cycles of the present invention, the catalyst undergoes an oxidation according to Equation II. (M=a transition metal)

$$MO_n + \tfrac{1}{2}xO_2 \rightarrow MO_{n+x} \qquad (II)$$

as for Example:

$$Cr_2O_3 + 1.5O_2 \rightarrow 2CrO_3 \qquad (IIa)$$

This oxidation yields an enthalpy change of $-17.0$ Kcal/mole at 1,100° F.

During reduction, the oxidized catalyst undergoes the reaction depicted in Equation III, $$MO_{n+x} + 2xH \rightarrow MO_n + xH_2O \qquad (III)$$

as for Example:

$$2CrO_3 + 3H_2 \rightarrow Cr_2O_3 + 3H_2O \qquad (IIIa)$$

undergoing an enthalpy change of $-43.7$ Kcal/mol at 1,100° F. Thus, the total enthalpy change for a complete oxidation/reduction cycle of the example is $-60.7$ Kcal/mol at 1,100° F.

Figure 5:
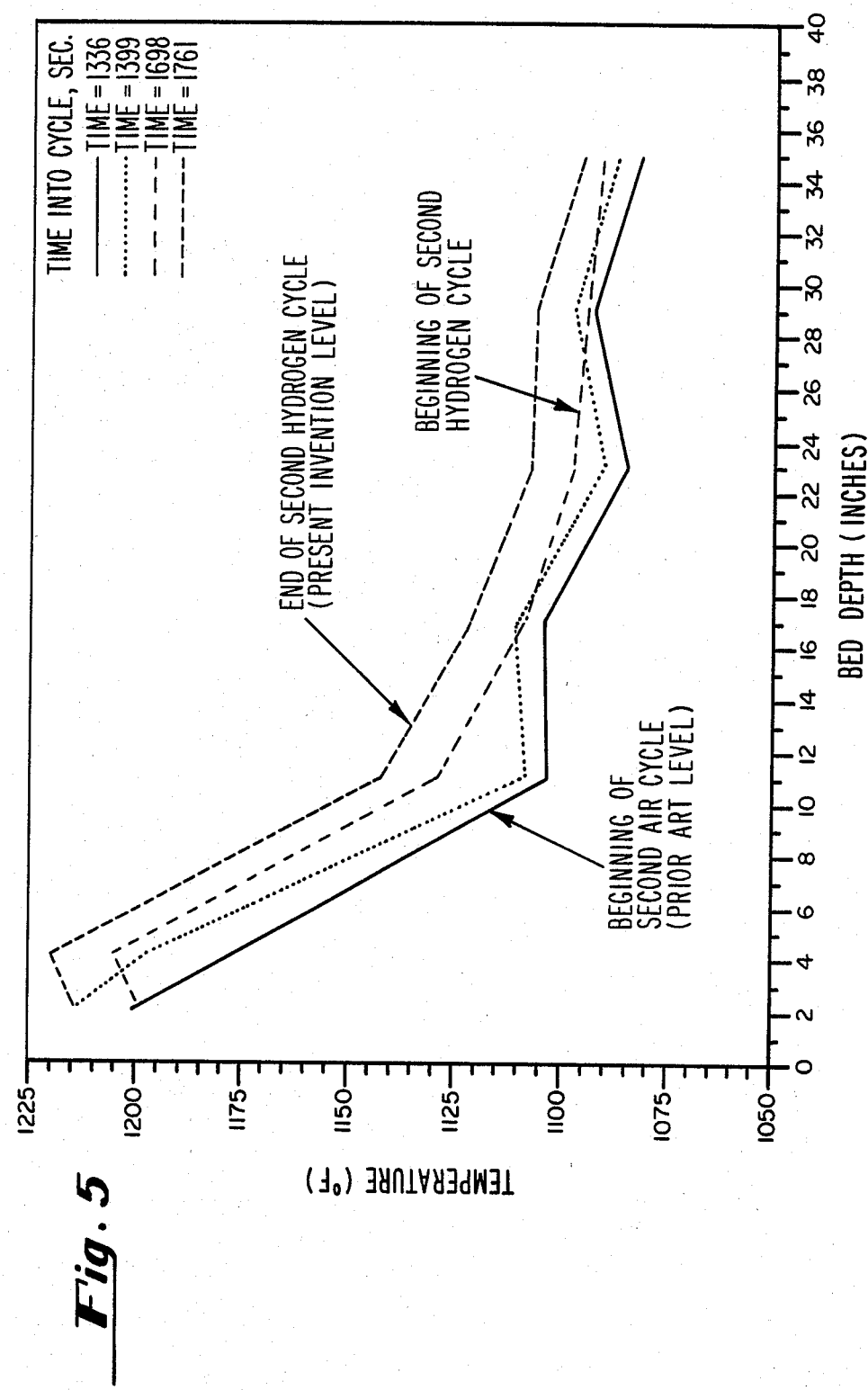
FIG. 5 is a graphic plot depicting the temperature profile of the catalytic bed operated according to the prior art and also according to the present invention.

Referring now to FIG. 5, which shows catalyst bed temperature profiles during reactor cycle, it is apparent that the energy yielded by the cyclic oxidation/reduction is distributed more evenly throughout the bed as the cycle intimately involves the catalyst itself. Thus, localized heating and resultant catalyst deactivation are reduced. Further, bed temperature gradients are reduced due to the catalyst's intimate involvement in the exothermic overall reaction of water formation. This reduction is thermal gradients contributes to overall process efficiency and yield. The additional benefit to be obtained by upflow hydrogen is evidenced by a higher bed temperature at the reactor outlet permitting higher overall kinetics and thermodynamic yield. This benefit would be most noticeable under partial reducing conditions. The present inventors have observed that catalyst reduction proceeds stepwise down through the reactor. For example, when hydrogen is initially passed down through the catalyst bed after an air reheating step, the top bed temperature increases first while the temperatures further down in the bed remain unchanged. With further addition of hydrogen the step change increase in temperature proceeds down through the reactor. By limiting the quantity of hydrogen or fuel gas used in the reduction steps and by passing this gas up through the catalyst bed (opposite direction to hydrocarbon feed and regeneration air flow), it would be possible to preferentially add heat to the bottom of the catalyst bed where it is most needed. This would smooth out the temperature profile and lower the maximum bed temperature required for a given olefin yield per pass.

In systems which produce limited amounts of coking of the catalyst bed, the present invention is superior in operation and efficiency to the burning of fuel gas in the reactor or to heating of the bed by the sensible heat of recycle air streams. The superiority of the present invention lies in its ability to heat the catalyst bed more evenly and more quickly (improving yields and lowering costs) than by prior art systems.

Figure 6:
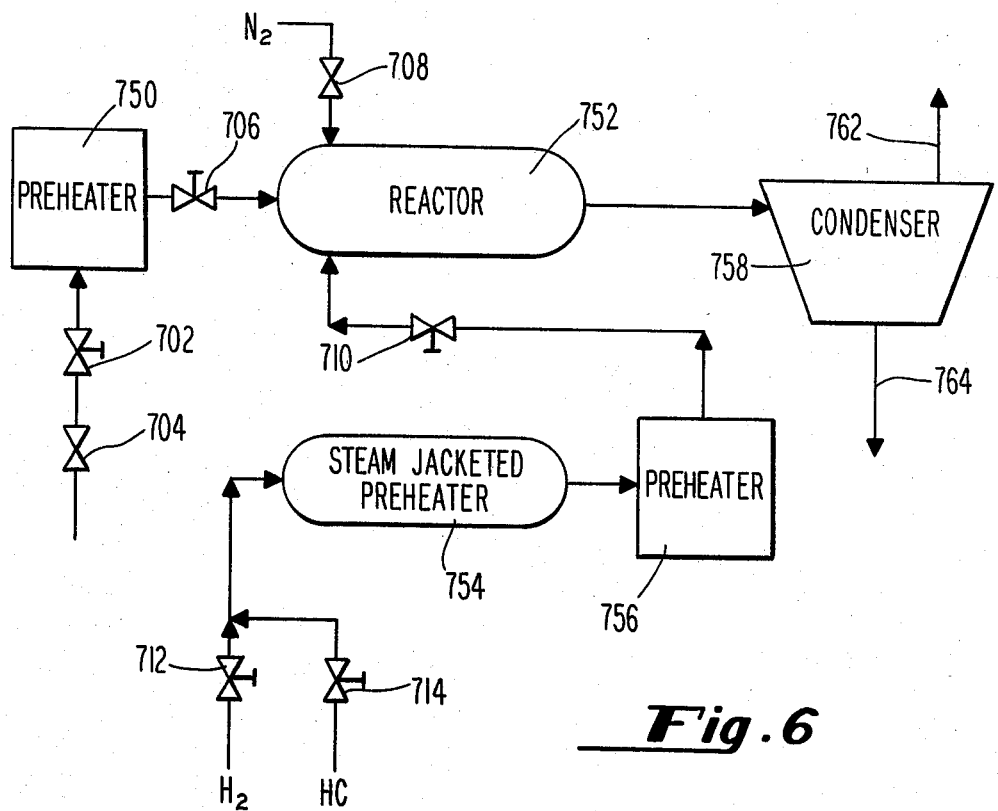
FIG. 6 is a block diagram of a pilot reactor employed for carrying out the present invention.

In assessing the performance parameters of the present invention, a pilot plant illustrated in FIG. 6 was operated in accordance with the reactor cycling method disclosed herein. The pilot unit of FIG. 6 comprises a reactor 752 which has a six-inch diameter × 36-inch deep fixed catalyst bed. Reactor 752 is supplied with preheated air from preheater 750 which is an electrically heated molten lead bath.

Hydrocarbons and hydrogen are also supplied to reactor 752 after preheating in steam-jacketed preheater 754 and preheater 756 which is an electrically heated bronze block. Reactor effluent is condensed in condenser 758. All gas supply lines to both the preheaters and the reactor are controlled by either manual or electrically operated valves. Reactor sequencing is controlled by a solid state sequence timer. In addition, all temperatures in the system are monitored by thermocouples and interconnected to an alarm system for orderly shut-down of the pilot unit in emergency situations. Product samples are analyzed by gas chromatography while air samples are analyzed by an infrared analyzer for carbon dioxide content.

Based upon calculations derived from pilot unit operations, the minimum amount of oxidizing gas required in each oxidation/reduction cycle is $4.5 \times 10^{-4}$ lb. mol of air per pound of catalyst containing about 18 wt% $Cr_2O_3$ while the minimum amount of reducing gas needed for every oxidation/reduction cycle is $1.8 \times 10^{-4}$ lb. mol of hydrogen per pound of the catalyst. These amounts of gas yield approximately 6.8 BTUs per pound of the catalyst for every complete oxidation/reduction cycle. It must be noted, however, that catalyst composition, age, and degree of deactivation must be considered in supplying gases during the oxidation/reduction cycles in the regeneration step.

While this invention has been described with reference to specific examples, it will nonetheless be understood by those skilled in the art that other variations of conditions and process parameters may be employed without departing from the spirit of the invention. It is intended that the claims which follow should be construed to encompass all such variations.

STATEMENT OF INDUSTRIAL UTILITY

The invention provides a process for the regeneration of catalytic dehydrogenation reactors useful in producing mono and diolefins from paraffins.

We claim:
1. A method of raising the catalyst bed temperature in a cyclic, adiabatic, catalytic dehydrogenation reactor after substantially all of the coke within said reactor has been combusted, said method comprising:
    (a) passing an oxidizing gas heated to 1000°–1300° F. through the reactor for a period of time sufficient to oxidize at least some of the catalyst and thereby add heat to the catalyst bed by the heat generated from said oxidation;
    (b) passing a reducing gas heated to 1000°–1300° F. through said reactor for a period of time sufficient to reduce the catalyst and thereby add heat to the catalyst bed by the heat generated from said reduction; and
    (c) repeating oxidizing step (a) and reducing step (b) for a predetermined number of cycles sufficient to heat said reactor to 1000°–1150° F.

2. The method of claim 1 wherein said oxidizing gas is air and said reducing gas is hydgrogen.

3. The method of claim 1 wherein said reactor is purged with steam prior to step (a).

4. The method of claim 1 wherein the duration of the final reducing step is adapted to optimize the oxidation state of the active component within said catalyst.

5. The method of claim 1 wherein the reducing gas is passed through the reactor in a direction opposite to the feed gas flow.

6. A method of raising the catalyst bed temperature in a cyclic, adiabetic dehydrogenation reactor after substantially all of the coke within the reactor has been combusted, said method comprising:

(a) passing an oxidizing gas heated to 1000°–1300° F. through said reactor for a predetermined period of time adopted to convert most of the active component within the catalyst from a first lower oxidation state to a first higher oxidation state and thereby add heat to the catalyst bed by the heat generated from said oxidation;

(b) passing a reducing gas heated to 1000°–1300° F. through said reactor for a predetermined period of time adapted to convert most of the active component from said first higher oxidation state to said first lower oxidation state and thereby add heat to the catalyst bed by the heat generated from said reduction; and (c) repeating oxidizing step (a) and reducing step (b) for a predetermined number of cycles sufficient to heat said reactor to 1000°–1150° F.

7. The method of claim 6 wherein said oxidizing gas is air.

8. The method of claim 6 wherein said reducing gas is hydrogen.

9. The method of claim 6 wherein the active component within the catalyst is a transition metal oxide.

10. The method of claim 6 wherein said active component within the catalyst is chromium oxide.

11. The method of claim 6 wherein the minimum amount of air supplied to the reactor in step (b) is $4.5 \times 10^{-4}$ lb-mol/lb catalyst containing 17–19 wt% $Cr_2O_3$ and the minimum amount of hydrogen supplied to the reactor in step (c) is $1.8 \times 10^{-4}$ lb-mol/lb catalyst containing 17–19 wt% $Cr_2O_3$.

12. The method of claim 6 wherein the reactor is purged with steam prior to step (a).

13. The method of claim 6 wherein the duration of the final reducing step (c) is adapted to optimize the oxidation state of the active component within the catalyst.

14. The method of claim 6 wherein said active component within the catalyst is chromium oxide.

15. The method of claim 6 wherein the reducing gas is passed through the reactor in a direction opposite to the feed gas flow.

* * * * *

UNITED STATES PATENT AND TRADEMARK OFFICE
CERTIFICATE OF CORRECTION

PATENT NO. : 4,581,339

DATED : April 8, 1986

INVENTOR(S) : B. L. Bhatt et al

It is certified that error appears in the above-identified patent and that said Letters Patent is hereby corrected as shown below:

Column 6, Line 66
  Delete "hydgrogen" and substitute therefor -- hydrogen --

Column 7, Line 8
  Delete "adiabetic" and substitute therefor -- adiabatic --

Signed and Sealed this

Twenty-first Day of October, 1986

[SEAL]

Attest:

DONALD J. QUIGG

Attesting Officer

Commissioner of Patents and Trademarks